United States Patent [19]
Greenfield et al.

[11] Patent Number: 5,248,480
[45] Date of Patent: Sep. 28, 1993

[54] APPARATUS FOR DRAWING FLUID SAMPLE AND COMPONENTS THEREOF

[75] Inventors: Walter Greenfield, Scarsdale, N.Y.; Edward G. Kearns, North Haven; James E. Kemble, Madison, both of Conn.

[73] Assignee: DiaSys Corporation, Waterbury, Conn.

[21] Appl. No.: 889,630

[22] Filed: May 28, 1992

[51] Int. Cl.$^5$ .............................................. B01F 11/00
[52] U.S. Cl. .............................. 422/68.1; 73/864.03; 73/864.74; 422/81; 422/100
[58] Field of Search .............. 422/100, 102, 101, 68.1, 422/81.0; 73/864.03, 864.02, 864.74; 210/515, 516, 518

[56] References Cited

U.S. PATENT DOCUMENTS

| | | | |
|---|---|---|---|
| 3,814,248 | 6/1972 | Lawhead | 210/83 |
| 3,835,710 | 9/1974 | Pogorski | 73/864.74 |
| 3,841,838 | 10/1974 | Natelson | 422/102 |
| 3,849,072 | 11/1974 | Ayres | 23/259 |
| 3,887,464 | 6/1975 | Ayres | 210/516 |
| 3,888,113 | 6/1975 | Miranda | 422/102 |
| 3,894,951 | 7/1975 | Ayres | 210/516 |
| 3,897,343 | 7/1975 | Ayres | 210/516 |
| 3,935,113 | 1/1976 | Ayres | 210/516 |
| 3,941,699 | 3/1976 | Hyres | 210/516 |
| 3,945,928 | 3/1976 | Ayres | 210/516 |
| 3,948,607 | 4/1976 | Atwood et al. | 23/259 |
| 4,037,464 | 7/1977 | Wenander | 422/100 |
| 4,055,501 | 10/1977 | Cornell | 210/516 |
| 4,209,256 | 6/1980 | Faulkner | 356/246 |
| 4,271,123 | 6/1981 | Curry et al. | 422/64 |
| 4,302,421 | 11/1981 | Baker | 422/64 |
| 4,308,028 | 12/1981 | Elkins | 23/230 |
| 4,312,591 | 1/1982 | Tomoff | 356/315 |
| 4,320,087 | 3/1982 | Chau et al. | 422/101 |
| 4,367,043 | 1/1983 | Sweet et al. | 356/338 |
| 4,393,466 | 7/1983 | Deindoerfer et al. | 364/415 |
| 4,448,752 | 5/1984 | Banno et al. | 422/81 |
| 4,464,254 | 8/1984 | Dojki et al. | 210/136 |
| 4,569,764 | 2/1986 | Satchell | 210/516 |
| 4,612,614 | 9/1986 | Deindoerfer et al. | 356/335 |
| 4,681,742 | 7/1987 | Johnson et al. | 422/100 |
| 4,804,267 | 2/1989 | Greenfield | 356/335 |
| 4,824,560 | 4/1989 | Alspector | 209/208 |
| 4,836,038 | 6/1989 | Baldwyn | 73/864.21 |
| 4,917,801 | 4/1990 | Luderer et al. | 210/516 |
| 4,981,654 | 1/1991 | Kuntz et al. | 422/102 |
| 4,983,038 | 1/1991 | Ohki et al. | 356/246 |

OTHER PUBLICATIONS

Baxter Catalog, "Nova Nucleus Modular Electrolyte-/Chemistry Analyzer", p. 203, Baxter Diagnostics Inc. IL, 1991.

Primary Examiner—James C. Housel
Assistant Examiner—Ramon Torres
Attorney, Agent, or Firm—St. Onge Steward Johnston & Reens

[57] ABSTRACT

An apparatus for drawing a specimen of a body fluid, such as urine from a sample tube. The specimen is drawn through a slide assembly for examination. A sample tube with a special plug and ball valve is described to provide a solids collection chamber with which a uniform amount of body liquid is provided for the specimen.

10 Claims, 5 Drawing Sheets

APPARATUS FOR DRAWING FLUID SAMPLE AND COMPONENTS THEREOF

FIELD OF THE INVENTION

This invention relates to an apparatus and technique for drawing a fluid specimen sample for analysis from a sample tube into a slide assembly and relates to a sample collection tube for use in such analysis. More specifically, this invention relates to an apparatus and technique for use in a urinanalysis.

BACKGROUND OF THE INVENTION

Systems and devices for urinanalysis are extensively used and practiced in clinics, laboratories and the like. With the increased presence of infectious diseases, such as AIDS, in biological materials, the need for safe systems and devices to minimize the handling of these potentially dangerous substances becomes evident. Urine sediment examination typically involves, as described in the U.S. Pat. Nos. 4,393,466 and 4,612,614, pouring of a sample into a tube which is then spun in a centrifuge to separate the sediment from its suspending fluid. After centrifugation, the cleared suspending fluid is poured out and the sediment resuspended in the remaining fluid. A sample of the resuspended sample must then be transferred to a microscopic slide for examination with a microscope. The '466 patent further describes a technique with which manual urine handling steps are eliminated and a video system is used to provide an electronic image of the urine specimen. A slide assembly is described which is shaped to provide a stable sample area where solid particles in the urine sample can be viewed.

Various other types of urine or other fluid sample supply devices are shown and described in the art, see for example, U.S. Pat. Nos. 4,302,421, 4,312,591, 4,367,043, 4,448,752, 4,836,038, 3,948,607, 4,209,256, and 4,271,123.

U.S. Pat. No. 4,804,267 to Walter Greenfield describes a urine sample analyzing system. A peristaltic pump is used to alternately pull a urine sample or a flushing fluid through a slide assembly. A video display system is employed to investigate solids in the sample.

The various urinanalysis systems tend to be complex and do not provide an inexpensive and convenient approach to the handling of urinanalysis in laboratories where complex fully automated systems cannot be justified.

In the evaluation of urine, it is at first necessary to concentrate the solids in a centrifuge operation, but then the solids should be resuspended. In order to achieve a reasonably consistent basis for analysis, the resuspension should be carried out with the same volume of urine. The conventional centrifuge tube, however, does not lend itself for such consistent analysis.

Various collection tubes have been proposed for extracting, separating or otherwise segregating components from a body fluid. For example, U.S. Pat. No. 3,818,248 describes a collection tube with which different phases of a fluid are separated. The device includes a movable sealing element or "traveling spool" which divides a test tube into an upper chamber and a lower chamber which has a floating plug. This device can serve the function described but does not permit the collection of a fixed or constant volume or urine.

U.S. Pat. No. 4,824,560 describes a urine centrifuge tube containing a partition that is shaped to promote the collection of solids in a lower chamber during centrifuge. The partition is pierced by a bore whose cross-section is less than 10 mm. and preferably not more than 5 mm. and is described even as a capillary bore. Even though the tube can yield a collection of solids in a lower chamber, during the decanting of excess liquid from the upper chamber, liquid from the lower chamber would tend to escape as well. This is particularly a problem with larger bore sizes while with a capillary bore, it is difficult to remove a consistent sample. Furthermore, no device is shown to facilitate the break-up for resuspension of consolidated solids.

Other body liquid collection tubes, some for centrifuge operations, are described in U.S. Pat. Nos. 4,464,254, 4,308,028, 4,055,501, 3,935,113, 3,945,928, and 3,849,072. These patents describe devices with similar drawbacks.

SUMMARY OF THE INVENTION

With an apparatus in accordance with the invention, a urine sediment analysis can be performed in a hygienic, efficient, and consistent manner while using an available microscope and a reusable slide assembly.

This is achieved with one apparatus in accordance with the invention by using a special urine collection tube, a slide assembly that can be irrigated with a flush solution and easily mounted on a microscope, and a compact fluid control device with which a urine sample can be drawn by a pump from the tube through the slide assembly and subsequently flushed back into the tube with a flushing liquid.

A plurality of urine samples can be rapidly and efficiently sampled in an efficient manner. A housing is provided on which a plurality of special centrifuge tubes are removably mounted for processing. A centrifuged urine sample containing tube is temporarily mounted at a test station where a needle is extended into the tube and into a solids collection chamber where solids have congregated and have been resuspended in a substantially constant volume.

A control is then actuated with which a sample from the solids collection chamber is drawn up through the slide assembly to a place that is between it and the housing for the apparatus of this invention. Upon completion of the microscopic examination, the control is again actuated so that the pump can be reversed and flushing liquid pumped from the reservoir through the slide assembly into the centrifuge tube.

With an apparatus in accordance with the invention, manual exposure to body fluid samples is significantly reduced, a rapid handling and safe examination of samples can be achieved and consistent examination results are achieved.

The consistency is particularly enhanced by maintaining a constant sample holding volume in the centrifuge sample collection tube. This is obtained by employing a plug in a centrifuge tube that is held in a fixed position in the tube so as to define a solids collection chamber between the plug and the closed bottom end of the tube. The plug has a bore through which solids can pass through into the solids collection chamber during a centrifuge operation. The bore terminates in the latter chamber in a valve seat and a loose-fitting valve element is located inside the chamber. The valve element has a sufficiently high specific gravity so that it will not float and solids can pass through the bore into the collection chamber.

However, at the conclusion of the centrifuge operation, the excess fluid can be decanted by inversion of the tube without a significant loss of fluid from the solids collection chamber since the valve element will automatically close the through bore by moving onto the valve seat.

With a submerged valve element loose in the collection chamber, any solid sediments that may have aggregated into a consolidated mass can be conveniently loosened and resuspended throughout the fluid in the collection chamber. This involves a gentle shaking of the tube in a manner whereby the valve element can break up consolidated sediments and resuspend the solids in a substantially constant volume of liquid.

It is, therefore, an object of the invention to provide an apparatus with which body fluids can be conveniently, safely, and expeditiously handled for analysis. It is a further object of the invention to provide a body fluid collection tube within which body fluids can be centrifuged and heavier components segregated and conveniently extracted in a consistent manner.

These and other objects and advantages of the invention can be understood from the following detailed description of an apparatus and collection tube in accordance with the invention and as illustrated in the drawings.

DETAILED DESCRIPTION OF DRAWINGS

Figure 1:
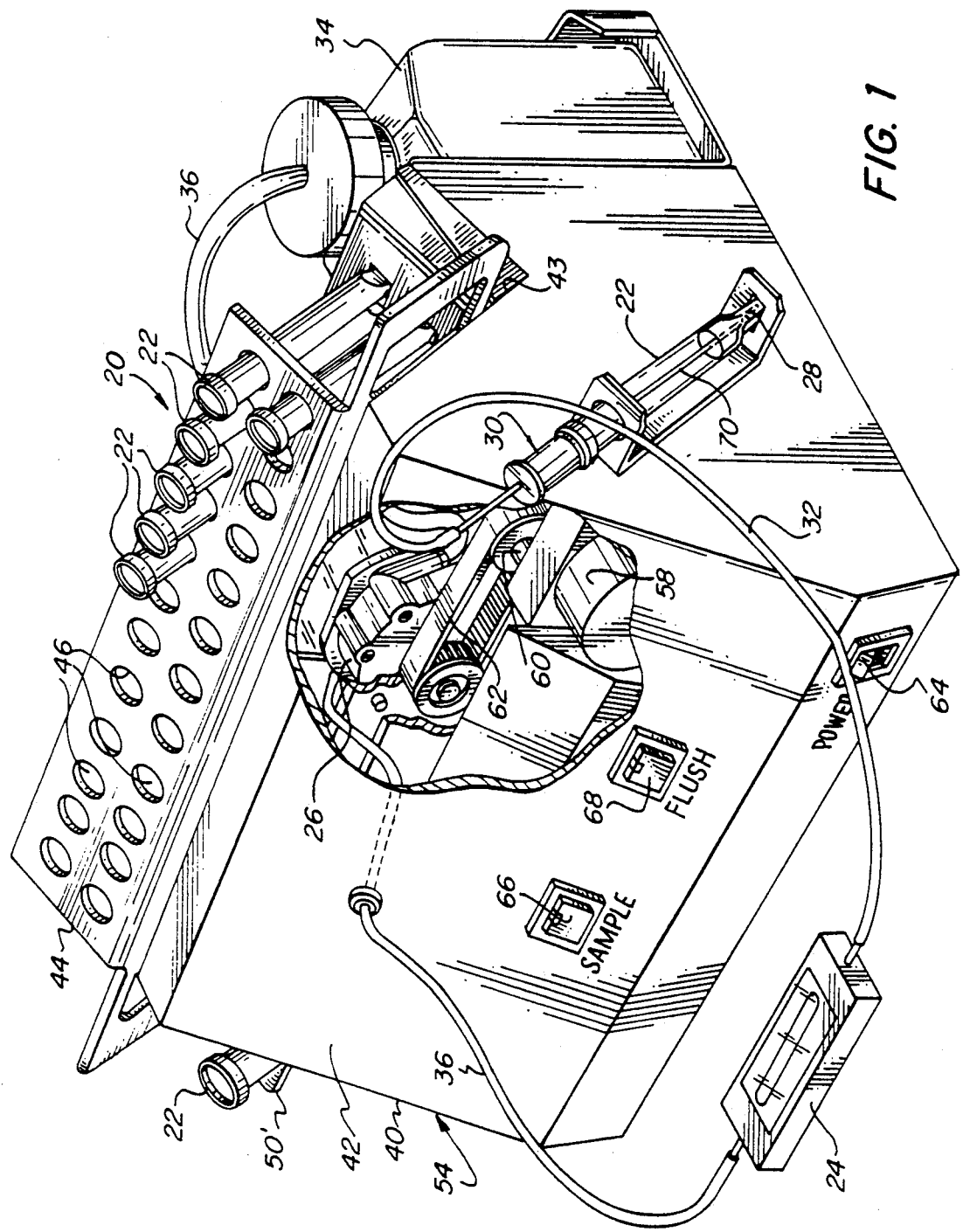
FIG. 1 is a front perspective, partially brokenaway view of a body fluid handling apparatus in accordance with the invention.
Figure 2:
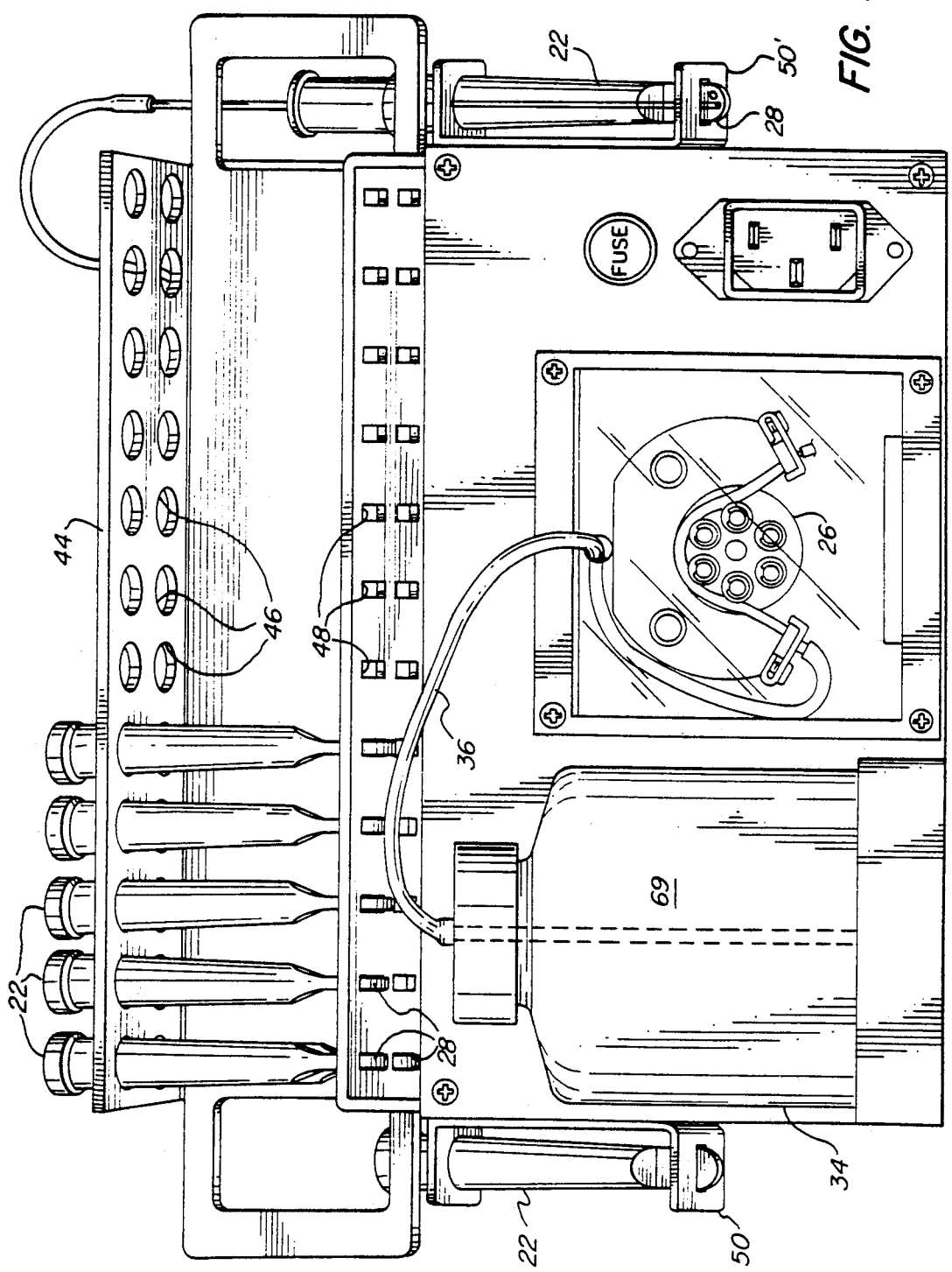
FIG. 2 is a rear view in elevation of the apparatus of FIG. 1.
Figure 3:
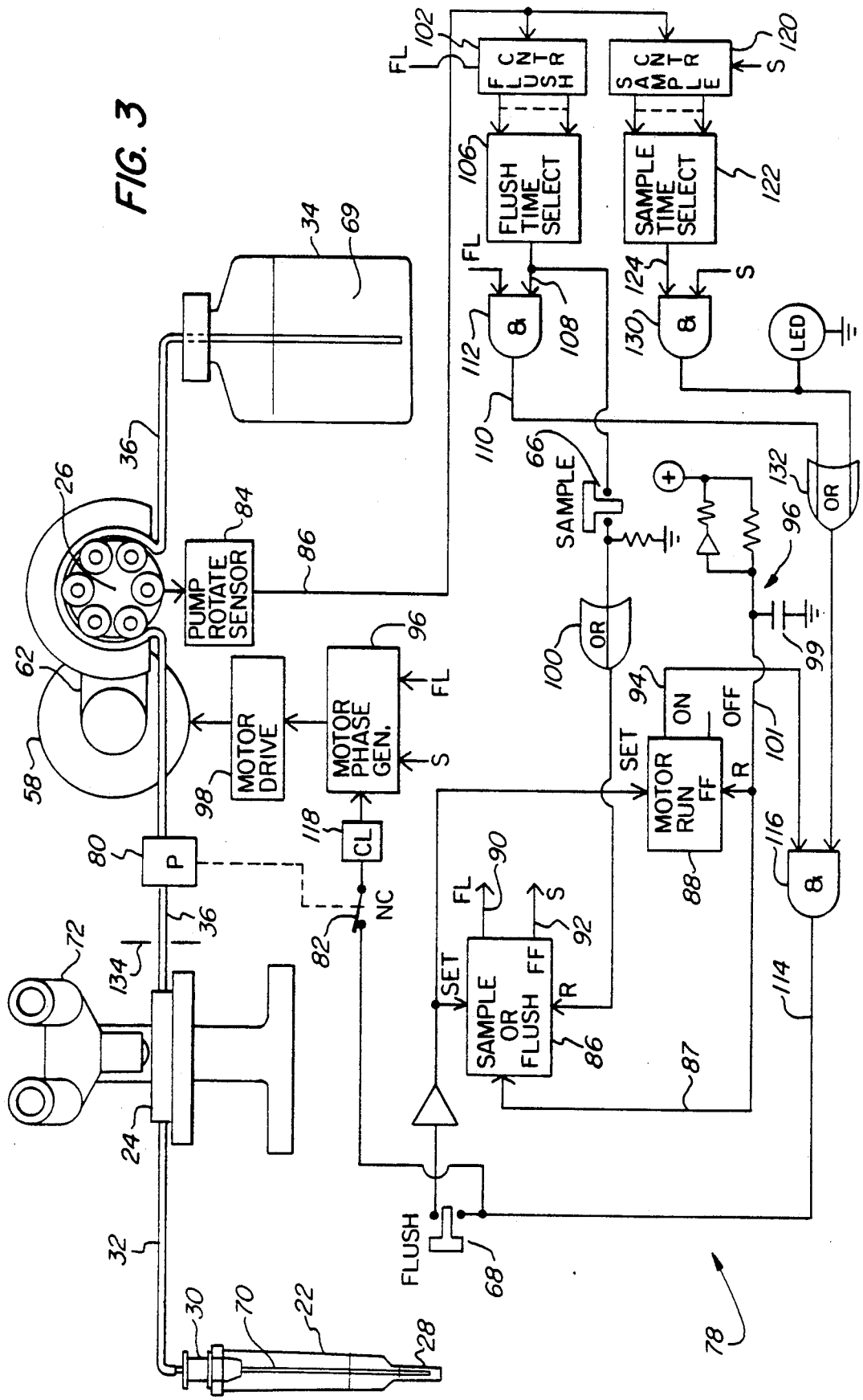
FIG. 3 is a block diagram and schematic view of the apparatus of FIG. 1.
Figure 4:
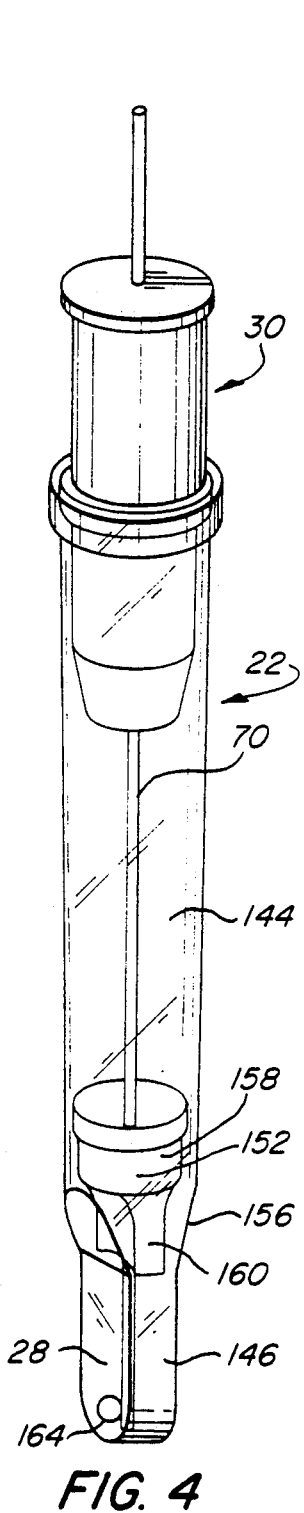
FIG. 4 is a front view in elevation of a urine sample collection and centrifuge tube in accordance with the invention.
Figure 5:
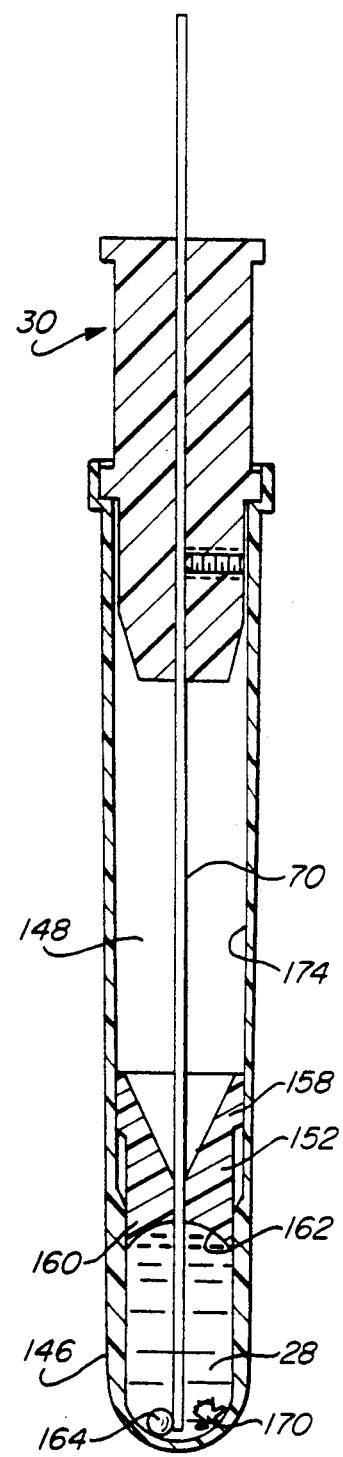
FIG. 5 is a cross-sectional view of the collection tube shown in FIG. 4.
Figure 6:
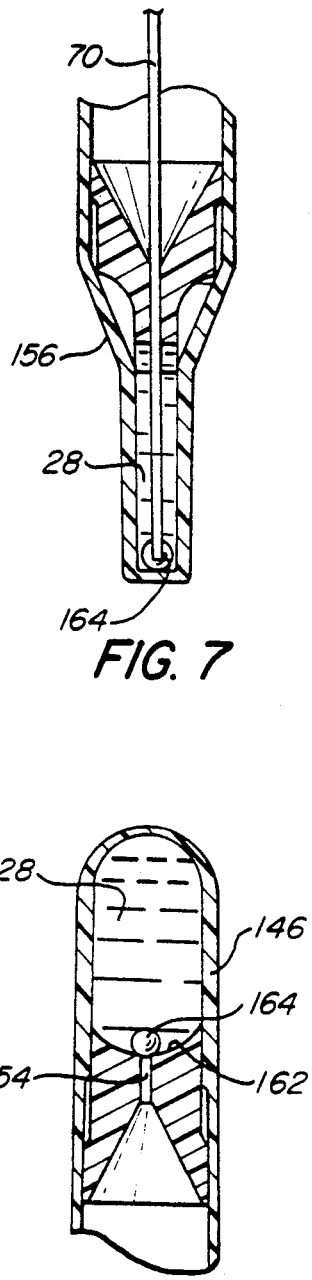
FIG. 6 is a bottom view of the collection tube of FIG. 5.
Figure 7:
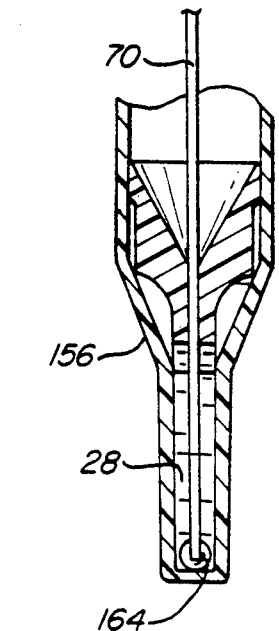
FIG. 7 is a partial, side cross-sectional view of the collection tube of FIG. 5.

With reference to FIGS. 1-3, an apparatus 20 is shown with which a urine sample is drawn from a collection and centrifuge tube 22 and pulled through a slide assembly 24. The apparatus 20 includes a peristaltic pump 26 which is reversible so that with one direction of rotation, a sample of urine is drawn from a solids collection chamber 28 in tube 22 through a needle assembly 30, and a flexible tube 32 into slide assembly 24. When the pump 26 is reversed, it draws a flushing liquid from a reservoir 34 and tubing 36 back to the collection tube 22. This is done for a sufficient length of time to flush the urine sample with its solids out of tubing 36, slide assembly 24, and tubing 32 and the needle assembly 30 into the collection tube 22. A quick connect-disconnect fitting 37, which is mounted on front panel 42, is interposed in tubing 36. This permits an easy replacement of slide assembly 24 and/or tubing 36 if severe contamination or damage occurs.

The apparatus 20 has a housing 40 with a sloped front panel 42 and a rack 44 on a top panel 43. The top panel is shaped to form a catchment 45 for spillage from sample tubes. The rack 44 has a plurality of suitably-aligned apertures 46, 48 so as to stably retain a plurality of collection tubes 22. Single tube holding racks 50, 50' are located on side panels 52, 54 to, for example, enable the apparatus to be used in a left or right-handed mode.

Housing 40 further includes an electrically controlled reversible stepper motor 58 whose output shaft 60 is coupled by a belt drive 62 to rotate peristaltic pump 26. Housing 40 further includes a suitable power supply and electric circuitry as more particularly described with reference to FIG. 3.

In addition to a power control switch 64, the front panel 42 has pushbutton switches 66, 68 which respectively control the start of a sample handling and a flushing phase.

In the sample phase, a collection centrifuge tube, such as 22, contains a urine sample in lower solids collection chamber 28. The needle assembly includes an elongate hollow needle 70 which extends into chamber 28 and is connected to flexible tubing 32. As pushbutton 66 is actuated, the pump 26 is rotated in a direction and in an amount sufficient to pull a liquid sample through the needle 70 and slide assembly 24 but not so far as to enter the front panel on apparatus housing 40.

The slide assembly 24 which is mounted on a suitable microscope 72 can then be optically examined.

When the examination is completed, the flush pushbutton 68 is actuated. This causes a reversal of the motor 58 in a direction whereby flushing liquid 69 is sucked from reservoir 34 and driven through tubings 36, and slide assembly 24, tubing 32, and needle assembly 30 into the collection tube 22.

The flushing actuation prepares slide assembly 24 and the connected tubings and needle for the next urine sample inside another collection tube 22. The entire process of handling of a urine sample for examination can be done in a short time and minimizes direct exposure by the operator to the body fluid.

FIG. 3 illustrates a control logic 78 used to operate apparatus 20. A pressure sensor 80 is placed in communication with flexible tubing 36 between fitting 37 and pump 26 to sense excessive pressures in the tubing such as may arise from a blocked probe 70 or an occluded tubing 32. A normally closed switch 82 is controlled by pressure sensor 80 and is located so as to interrupt drive to the motor 58. A pump rotation sensor 84 is used to generate pulses on line 86 representative of pump rotation and thus in effect representative of either the volume of sample liquid being drawn from collection tube 22 or the volume of flushing liquid 69 being pumped.

A pair of control flip-flops 86, 88 are employed to regulate the operation of pump 26. Flip flop 86 sets either sample or flush phases with its outputs 90, 92 respectively labeled S and FL. Flip flop 88 regulates the activation of reversible stepper motor 58 by way of "on" output 94.

The motor direction of rotation is controlled by a motor phase generator 96 which generates appropriately phased motor drive signals with a shift register enabled by the sample and flush phase signals S and FL. The motor phase signals are amplified by a motor drive 98.

The control 78 responds to a power on condition by forcing the phase control flip flop 86 into a flush mode and the motor run flip flop 88 in the OFF state. This can be achieved by a direct coupling with a line 87. A network 96 is provided and includes a capacitor 99 whose initial low voltage during turn-on assures that the motor run control flip flop 88 is in the OFF state. In this manner, the system must first activate a flushing operation before a sample can be drawn from a solids collection chamber 28 in tube 22.

When the flush control switch 68 is activated, the motor phase generator 96 generates appropriately phased pulses to stepper motor 58 to cause pump 26 to draw flushing liquid 69 from reservoir 34. As pump 26 rotates, sensor 84 generates pulses which are applied to a flush phase counter 102. A flush time selection network 106 is connected to counter 102 and generates, on output line 108 an enabling signal commensurate with the desired amount of flushing liquid to be pumped from reservoir 34 back into tube 22. Network 106 can be a decode network with dip switches to enable one to manually select the number of sensor pulses on line 86 needed to complete the flushing phase.

The output 108 from the flush select network 106 causes, in the flush phase, an output on line 110 from an AND gate 112 to in turn deliver a motor enabling signal on output 114 of gate 116 since the signal on line 94 was activated by flush control switch 68. The motor enabling signal is applied through pressure-control switch 82 to an enabling input of a clock 118 used to initiate the generation of motor drive pulses from motor phase generator 96.

If no excessive pressures occur in tubing 36, the motor 58 continues in its flushing direction until counter 102 reaches the count at which the flushing selection network 106 causes a cessation of the enabling signal on line 108. This removes the enabling signal to clock 118 and stops the motor 58.

At this time, the output on line 108 is in an active state for the sample control switch 66. Hence, when the sample push button 66 is activated, flip flop 86 is set in the sample mode. This enables a sample pulse counter 120 which counts pulses on line 86 from the pump rotation sensor 84.

The sample time selection network 122 produces an output on line 124 which acts through AND gate 130, OR gate 132, and gate 116 to energize clock 118. The sample phase generator 96 now produces pulses to drive motor 58 in a direction whereby pump 84 draws a sample from tube 22.

The duration of the sample rotation is controlled by the sample selection network 122. This is set, such as with dip switches, to extract a liquid sample from solids chamber 28 sufficient to extend through tubing 32 past slide assembly 24, but not so far as to reach the reservoir 34. Hence, preferably up to about a region indicated by line 134.

Figure 9:
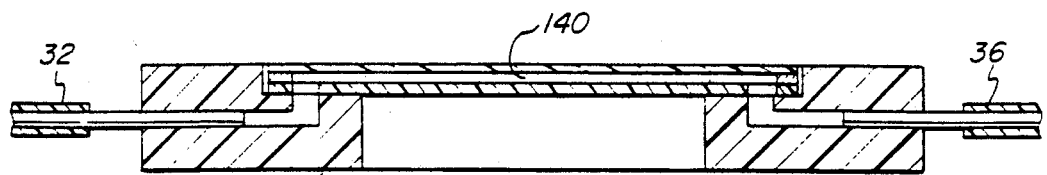
FIG. 9 is a side cross-sectional view of a slide assembly for use with an apparatus as shown in FIG. 1.

FIG. 9 illustrates a cross-section of the slide assembly 24. This includes a small volume transparent viewing chamber 140 which is adapted to enable viewing of a sample with the microscope as shown in FIG. 3.

An important feature of the invention involves use of a sample collection and centrifuge tube 22 with which a uniform sample can be conveniently obtained. This involves, as illustrated for one tube 22 of this invention in FIGS. 4–8, a sample collection tube 22 with a cylindrical upper body 144 and a transparent lower flattened body 146. The upper body encloses a chamber 148 which is separated from a lower-located solids collection chamber 28 by a plug 152. A bore 154 extends through plug 152 so that small solids can, during a centrifuge operation, pass through bore 154 into chamber 28.

Plug 152 is shaped so that it is seated in a fixed position between chambers 148, 28 at the transition section 156 of tube 22. The upper portion 158 of plug 152 has a larger cross-section than its lower portion 160 which extends slightly into chamber 28. The through bore 154 terminates at portion 160 which is shaped to form a valve seat 162 for a freely-moving small ball valve 164 which is captured within chamber 28. Valve seat 162 can be concave or V-shaped or such other shape as is desirable to form a valve seat. Ball valve 164 has a specific gravity that is sufficiently high so as not to float inside chamber 28 and thus normally rest on the bottom of chamber 28. For urine collection and centrifuge, a specific gravity greater than one is needed.

Figure 8:
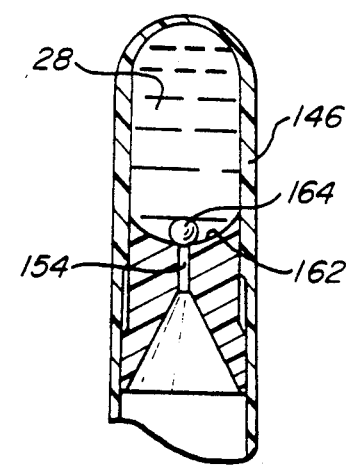
FIG. 8 is a partial, front cross-sectional view of the collection tube as shown in FIG. 5 but in an inverted position.

During a centrifuge operation, the needle assembly 30 is not present. The solids in the urine specimen are forced through bore 154 into the lower chamber 28. At the end of the centrifuge, excess liquid is in the upper chamber 148 and solids have aggregated into a consolidated mass in the lower chamber 28. The excess liquid in the upper chamber can be decanted, without loss of liquid from the lower chamber 28, by sufficiently inverting the tube 22, as illustrated in FIG. 8. This shows the ball valve on the valve seat 162, resulting in the retention of a fixed volume of liquid in chamber 28.

When tube 22 is placed upright again, ball valve 164, which has a sufficient mass, can be used with a gentle agitation of tube 22, to break up any consolidated solids in mass 170 and cause them to be resuspended. Since the resuspension occurs within a consistent volume of liquid inside chamber 28, the density of solids can be more accurately determined from the microscopic investigation.

Figure 16:
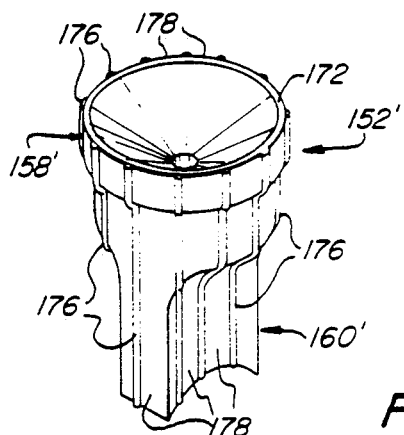
FIG. 16 is a perspective view of a modified separator plug for use in a collection tube as illustrated in FIG. 5.
Figure 10:
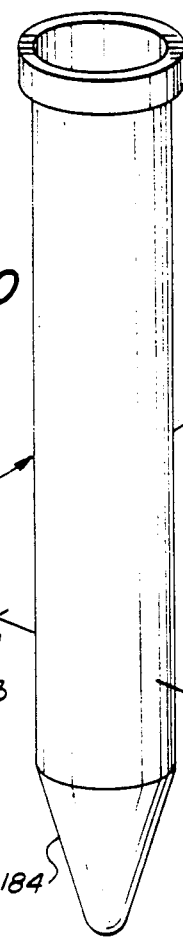
FIG. 10 is another centrifuge and solids collection tube in accordance with the invention.

During a centrifuge operation, solids tend to collect at the small ledge formed between the upper edge 172 of the plug 152 and the inner wall 174 of upper chamber 148. Hence, as shown in FIG. 16 in a preferred form of a plug 152', its upper edge 172 is made as small as possible and is spaced away from wall 174 by use of longitudinally-extending ribs 176. These ribs provide thin, capillary-sized, passages 178 around the periphery of plug 152. Passages 178 are sufficiently wide to allow solids to pass through to the collection chamber 28, yet not so wide as to allow liquid to escape when the excess liquid in chamber 148 needs to be decanted.

FIGS. 10-13 illustrate another centrifuge and solids collection tube 180. The tube 180 can be of conventional shape with a wide upper body 182 and a conical lower body 184. A plug 186 is provided with an upper portion 188 shaped to snugly fit inside the upper body 182 and a lower portion 190 that extends slightly into the lower body 184. Ribs 192 extend along the outer surface of plug 186 to form capillary-sized passages 194 between the ribs for passage of centrifuged solids.

Plug 186 has a through bore 196 and valve seat 198 facing a solids collection chamber 200. A ball valve 164' is located in chamber 200.

Figure 14:
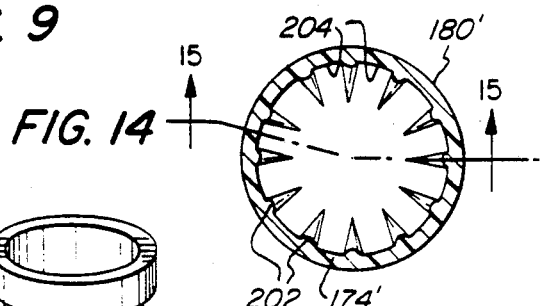
FIG. 14 is a cross-sectional downward view of a solids collection tube, without a separator plug, but modified in accordance with the invention.
Figure 15:
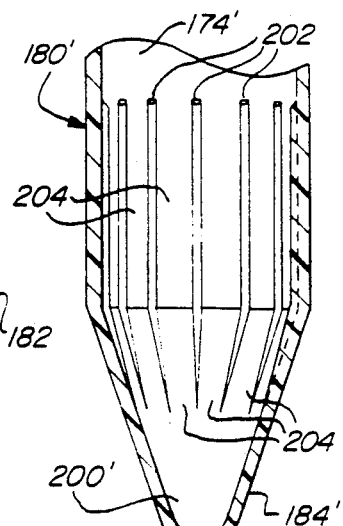
FIG. 15 is a longitudinal cross-sectional view of the modified solids collection tube as shown in FIG. 14 and is taken along the lines 15—15 therein.
Figure 13:
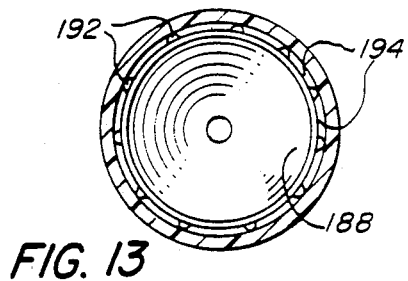
FIG. 13 is a cross-sectional view of the collection tube of FIG. 10 and is taken along the line 11—11 therein.
Figure 11:
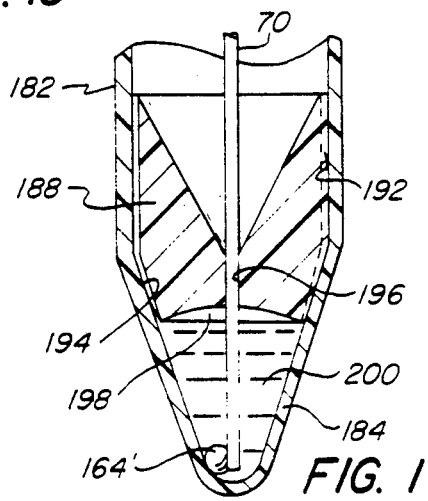
FIG. 11 is a partial longitudinal section view of the solids collection tube of FIG. 10.
Figure 12:
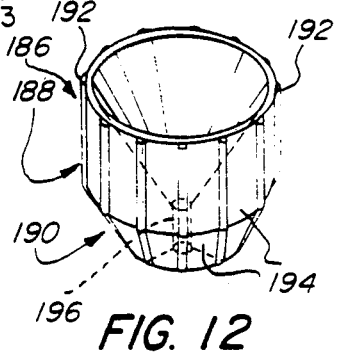
FIG. 12 is a perspective view of a separator plug used in the collection tube of FIG. 10.

In an alternate form of a solids collection tube in accordance with the invention as shown in FIGS. 14 and 15, ribs 202 similar to ribs 176 in FIG. 16 or 192 in FIG. 12 are placed on the inside wall 174' of tube 180. The ribs are integrally molded with the tube 180 by adding appropriately-shaped recesses to an injection molding die used to make tubes such as 180. The spaces 204 between ribs 202 then form, with an appropriately outer smooth-walled plug such as 186 desired longitudinal capillary passages.

Having thus described illustrative forms of the invention, its advantages can be appreciated. Variations from the described embodiment can be made without departing from the scope of the invention.

What is claimed is:

1. An apparatus for drawing a fluid sample for analysis through a slide assembly comprising:
   a solids collection tube for holding a fluid sample;
   a flushing fluid containing reservoir;
   reversible pump means for pumping fluid in either direction between the solids collection tube and the flushing tube containing reservoir;
   a slide assembly having a viewing chamber through which a fluid sample can be viewed, and further having a first port and a second port in fluid flow communication with the viewing chamber;
   tube means for coupling, the reservoir to the reversible pump means, the pump means to one of the ports of the slide assembly, and the slide assembly's other port to the solids collection tube;
   means for activating the reversible pump means in one operative direction only for a sufficient time so as to cause a fluid sample from the solids collection tube to be drawn through the slide assembly without passing into the flushing fluid containing reservoir; and
   means for activating the reversible pump means in another operative direction so as to cause flushing fluid from the flushing fluid containing reservoir to pass through the slide assembly for a sufficient time to return the fluid sample to the solids collection tube and flush the slide assembly and the tube means.

2. The apparatus as claimed in claim 1, wherein said means for activating the reversible pump includes:
   means for sensing pump activity and producing a pump signal indicative thereof;
   means responsive to the pump signal for alternatively generating a flush enabling signal representative of the amount of flushing fluid to be pumped and a sample enabling signal representative of the amount of sampling fluid to be drawn from the solids collection tube.

3. The apparatus as claimed in claim 2 wherein the means for alternately generating the flush and sample enabling signals includes:
   a panel mounted flush control switch coupled to initiate a pump activity in a flushing direction; and
   a panel mounted sample control switch coupled to initiate a pump activity in a fluid sample drawing direction which is opposite to said flushing direction.

4. The apparatus as claimed in claim 1 and further including a housing having a front panel and a rear panel, and a tube rack mounted to the rear panel and having a plurality of holes sized to retain a plurality of collection tubes.

5. The apparatus as claimed in claim 4 wherein the housing has side panels, and a tube holder mounted to at least one of said side panels to retain a solids collection tube.

6. The apparatus as claimed in claim 1 and further including a needle assembly shaped to be releasably mounted inside a solids collection tube.

7. An apparatus for drawing a sample of test fluid through a slide assembly for analysis with a microscope, comprising:
   a collection tube for holding said test fluid;
   a flushing fluid supply;
   pump means in fluid flow communication with said flushing fluid supply for pumping fluid between the collection tube and the flushing fluid supply;
   reusable slide assembly means having a viewing chamber for holding a fluid sample to enable direct viewing of the sample by the microscope; said slide assembly means being removeably mountable to the microscope; said slide assembly means further having a first port and a second port in fluid flow communication with the viewing chamber,
   tube means for coupling the test fluid from the collection tube to the first port of the reusable slide assembly means and for coupling the second port of the reusable slide assembly means to the pump means;
   means for activating the pump means in a first operative direction only for a sufficient time so as to draw a sample of test fluid from the collection tube through the viewing chamber of the slide assembly means without passing into the flushing fluid supply; and
   means for activating the pump means in a second operative direction for pumping flushing fluid from the flushing fluid supply through the viewing chamber to flush the test fluid sample therefrom into said collection tube.

8. The apparatus as claimed in claim 7 wherein the tube means includes a needle assembly and a flexible tube connected thereto, said needle assembly being adapted to mount to a collection tube to extract said sample of test fluid and reinsert said sample with flushing fluid into the collection tube after examination of the sample with the microscope.

9. The apparatus as claimed in claim 7 wherein said means for activating said pump means in said first operative direction includes means for controlling the time said pump means is operated to extract said sample so as to avoid pumping test fluid into said flushing fluid supply.

10. The apparatus as claimed in claim 7 and further including means for sensing fluid pressure in the tube means between the slide assembly and the pump means for producing a pressure signal, and
   means responsive to said pressure signal for interrupting operation of said pump means when said pressure becomes excessive.

* * * * *